(12) United States Patent
Ota et al.

(10) Patent No.: US 10,114,087 B2
(45) Date of Patent: Oct. 30, 2018

(54) RF COIL AND MAGNETIC RESONANCE IMAGING APPARATUS

(71) Applicant: TOSHIBA MEDICAL SYSTEMS CORPORATION, Otawara-shi (JP)

(72) Inventors: Miyuki Ota, Otawara (JP); Sadanori Tomiha, Otawara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 274 days.

(21) Appl. No.: 14/879,730

(22) Filed: Oct. 9, 2015

(65) Prior Publication Data

US 2016/0033589 A1  Feb. 4, 2016

Related U.S. Application Data

(63) Continuation of application No. PCT/JP2014/060428, filed on Apr. 10, 2014.

(30) Foreign Application Priority Data

Apr. 10, 2013 (JP) .................. 2013-082135

(51) Int. Cl.
*A61B 5/055* (2006.01)
*G01R 33/28* (2006.01)
*G01R 33/3415* (2006.01)
*G01R 33/34* (2006.01)
*A61B 90/11* (2016.01)
*A61B 10/04* (2006.01)
*A61B 17/34* (2006.01)

(52) U.S. Cl.
CPC ............ *G01R 33/285* (2013.01); *A61B 90/11* (2016.02); *G01R 33/34* (2013.01); *G01R 33/3415* (2013.01); *A61B 5/055* (2013.01); *A61B 2010/045* (2013.01); *A61B 2017/3411* (2013.01)

(58) Field of Classification Search
CPC ...... A61B 2010/045; A61B 2017/3411; A61B 5/055; A61B 90/11; G01R 33/285; G01R 33/34; G01R 33/3415
See application file for complete search history.

(56) References Cited

U.S. PATENT DOCUMENTS

| 5,678,549 | A | 10/1997 | Heywang-Koebrunner et al. |
| 2011/0241683 | A1 | 10/2011 | Nnewihe et al. |
| 2014/0213886 | A1* | 7/2014 | Menon ............... A61B 10/0275 600/411 |

FOREIGN PATENT DOCUMENTS

| JP | 6-181908 | 7/1994 |
| JP | 10-165403 | 6/1998 |

OTHER PUBLICATIONS

International Search Report for PCT/JP2014/060428, dated May 20, 2014, 5 pages.
Written Opinion (non-English) of the ISA for PCT/JP2014/060428, dated May 20, 2014, 3 pages.

* cited by examiner

*Primary Examiner* — Ruth S Smith
(74) *Attorney, Agent, or Firm* — Nixon & Vanderhye P.C.

(57) ABSTRACT

An RF coil includes a puncture needle insertion assembly in which a plurality of holes into which a puncture needle is inserted are formed within a surface of the puncture needle insertion assembly. In the puncture needle insertion assembly, conductors of a plurality of elements of a coil that are being insulated from one another are laid to meander on a frame between the holes.

9 Claims, 7 Drawing Sheets

DIRECTION IN WHICH PUNCTURE
NEEDLE IS INSERTED

DIRECTION IN WHICH PUNCTURE
NEEDLE IS INSERTED

DIRECTION OF
PLANE SURFACE

RF COIL AND MAGNETIC RESONANCE IMAGING APPARATUS

CROSS-REFERENCE TO RELATED APPLICATIONS

This application is a continuation of PCT international application Ser. No. PCT/JP2014/060428 filed on Apr. 10, 2014 which designates the United States, incorporated herein by reference, and which claims the benefit of priority from Japanese Patent Application No. 2013-082135, filed on Apr. 10, 2013, the entire contents of which are incorporated herein by reference.

FIELD

Embodiments described herein relate generally to an RF coil and a magnetic resonance imaging apparatus.

BACKGROUND

Magnetic resonance imaging is an imaging method in which the spins of atomic nuclei of a subject placed in a magnetostatic field are magnetically excited with radio frequency (RF) pulses with the Larmor frequency of the spins and an image is generated from the data of magnetic resonance signals generated in accordance with the excitation.

In this magnetic resonance imaging, biopsy may be performed. In biopsy, tissue is sampled from a subject and examined, and a puncture needle may be used to sample tissue. For example, when tissue of breast is sampled, in general, the subject is laid facing down on a breast RF coil and a puncture needle is inserted via an instrument that has a grid structure and that is disposed to adhere to a side surface of the breast. For example, a block for fixing the puncture needle is attached to a rectangular hole that is formed by the grid and the puncture needle being fixed by the block is caused to puncture the breast.

In imaging of a breast, it is preferable to dispose coil elements on a side surface of the breast; however, when the number of elements disposed at the side surface of the breast is increased for the purpose of, for example, parallel imaging, the elements partly block the area for puncture so that it is not possible to secure a sufficient puncture area. On the other hand, when elements are disposed around the outer circumference of the whole puncture area to prioritize securing of the puncture area, the diameter of the elements has to be increased, which lowers the performance of parallel imaging in accordance with lowering of the signal noise ratio (SNR) and accordingly extends the imaging time.

DETAILED DESCRIPTION

An RF coil includes a puncture needle insertion assembly in which a plurality of holes into which a puncture needle is inserted are formed within a surface of the puncture needle insertion assembly. In the puncture needle insertion assembly, conductors of a plurality of elements of a coil that are being insulated from one another are laid to meander on a frame between the holes.

With reference to the accompanying drawings, an RF coil and a magnetic resonance imaging apparatuses according to embodiments will be described below. Embodiments are not limited to the following embodiments. Furthermore, in principle, it is possible to apply the contents of the embodiments to be described below to other embodiments.

First Embodiment

Figure 1:
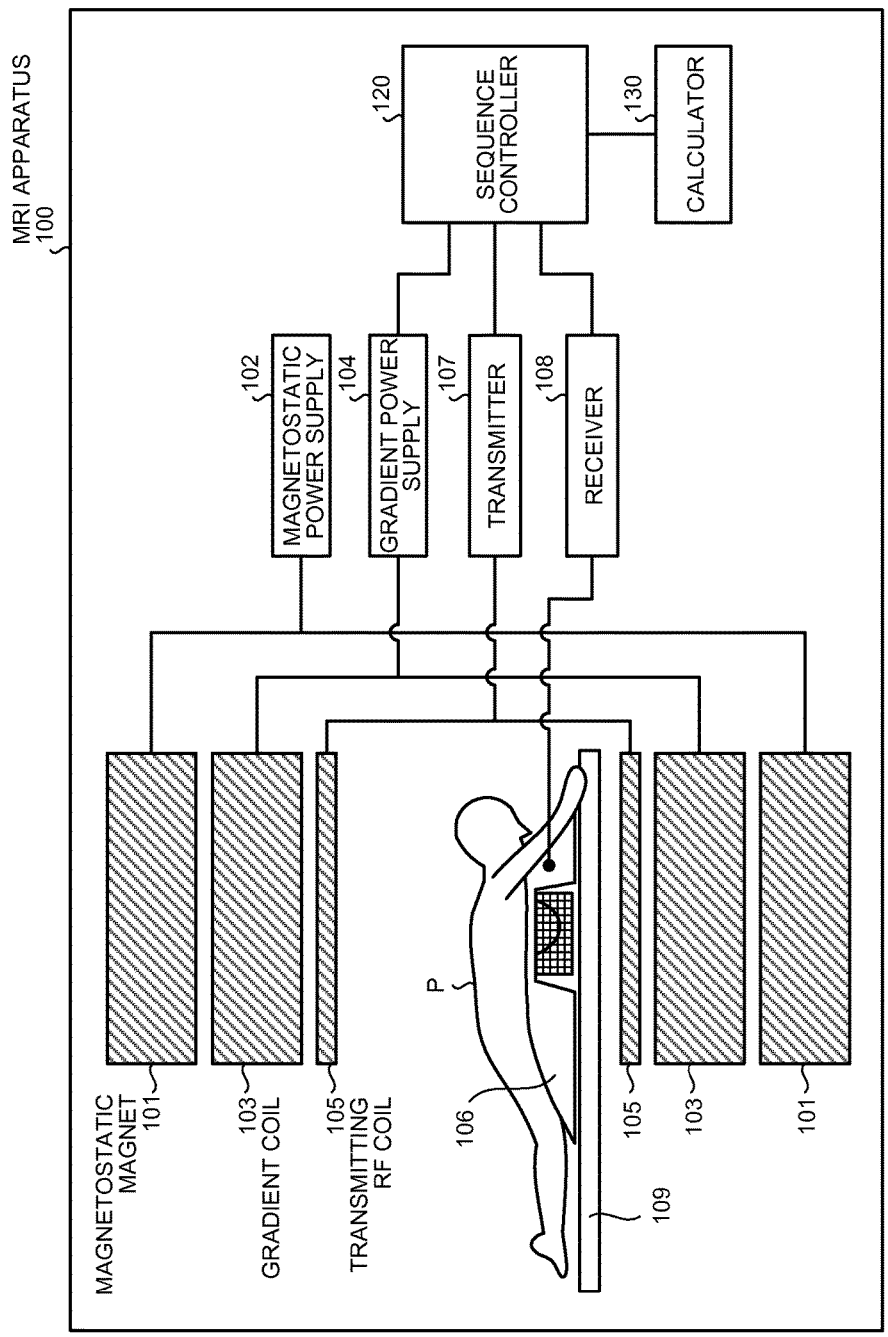
FIG. 1 is a functional block diagram showing a configuration of an MRI apparatus according to a first embodiment.

FIG. 1 is a functional block diagram showing a configuration of a magnetic resonance imaging (MRI) apparatus 100 according to a first embodiment. As shown in FIG. 1, the MRI apparatus 100 includes a magnetostatic magnet 101; a magnetostatic power supply 102; a gradient coil 103; a gradient power supply 104; a transmitting RF coil 105; a breast RF coil 106; a transmitter 107; a receiver 108; a couch 109; a sequence controller 120; and a calculator 130. The MRI apparatus 100 does not include a subject P (such as a human body). The configuration shown in FIG. 1 is an example only. Each unit may be configured integrally or separately.

The magnetostatic magnet 101 is a hollow magnet that is formed in a cylindrical shape and that generates a magnetostatic field in the internal space of the cylinder. The magnetostatic magnet 101 is, for example, a superconducting magnet that is excited with a current supply from the magnetostatic power supply 102. The magnetostatic power supply 102 supplies a current to the magnetostatic magnet 101. The magnetostatic magnet 101 may be a permanent magnet and, if so, the MRI apparatus 100 would not necessarily include the magnetostatic power supply 102. The magnetostatic power supply 102 may be provided separately from the MRI apparatus 100.

The gradient coil 103 is a hollow coil that is formed in a cylindrical shape and that is disposed at the inner side with respect to the magnetostatic magnet 101. The gradient coil 103 generates a gradient field upon receiving a current supply from the gradient power supply 104. The gradient power supply 104 supplies a current to the gradient coil 103.

The transmitting RF coil 105 is disposed at the inner side with respect to the gradient coil 103 and, upon receiving an RF pulse supply from the transmitter 107, generates a high-frequency magnetic field. The breast RF coil 106 receives a magnetic resonance (MR) signal that is generated from the subject P because of the effect of the high-frequency magnetic field and outputs the received MR signal to the receiver 108. The breast RF coil 106 will be described in detail below.

The combination of the above-described transmitting RF coil 105 and the breast RF coil 106 is an example only. It suffices if the RF coil be configured of any one of, or a combination of, a coil having only a transmitting function, a coil having only a receiving function, and a coil having transmitting and receiving functions. For example, the breast RF coil 106 may have transmitting and receiving functions.

The transmitter 107 supplies, to the transmitting RF coil 105, an RF pulse corresponding to a Lamor frequency that is determined according to the type of a targeted atom and the magnetic field intensity. The receiver 108 detects the MR signal that is output from the breast RF coil 106 and generates MR data based on the detected MR signal. Specifically, the receiver 108 generates MR data by performing digital conversion on the MR signal output from the breast RF coil 106. The receiver 108 transmits the generated MR data to the sequence controller 120. The receiver 108 may be provided at the side of the trestle device including the magnetostatic magnet 101 and the gradient coil 103.

The couch 109 includes a couchtop on which the subject P is placed. FIG. 1 only illustrates the couchtop for convenience of description. In general, the couch 109 is set such that its longitudinal direction is parallel to the center axis of the cylinder of the magnetostatic magnet 101. The couchtop is movable in its longitudinal direction and vertically. The couchtop is inserted into the internal space of the cylinder of the transmitting RF coil 105.

The sequence controller 120 images the subject P by driving the gradient power supply 104, the transmitter 107, and the receiver 108 according to sequence information transmitted from the calculator 130. The sequence information is information that defines a procedure for imaging. The sequence information defines the intensity of a current to be supplied from the gradient power supply 104 to the gradient coil 103, the timing at which the current is supplied, the intensity of the RF pulse supplied from the transmitter 107 to the transmitting RF coil 105, the timing at which the RF pulse is applied, and the timing at which the receiver 108 detects the MR signal. For example, the sequence controller 120 executes an imaging sequence for parallel imaging for acquiring MR signals by using multiple elements of the breast RF coil 106. Parallel imaging is a technology for performing imaging by using multiple elements with a number of samples smaller than that for full-sampling and for reconstructing an MR image by using the difference in sensitivity per element. For the parallel imaging technologies, for example, senility encoding (SENSE) and generalized auto calibrating partially parallel acquisition (GRAPPA) are widely known.

For example, the sequence controller 120 is an integrated circuit, such as an application specific integrated circuit (ASIC) or a field programmable gate array (FPGA), or an electronic circuit, such as a central processing unit (CPU) or a micro processing unit (MPU).

Upon receiving the MR data from the receiver 108 as a result of imaging the subject P by driving the gradient power supply 104, the transmitter 107, and the receiver 108, the sequence controller 120 transfers the received MR data to the calculator 130.

The calculator 130 controls the whole MRI apparatus 100. Furthermore, the calculator 130, for example, generates an MR image by performing reconstruction processing, such as the Fourier transform, on the MR data transferred from the sequence controller 120. For example, the calculator 130 includes a controller, storage, an input device, and a display. The controller is an integrated circuit, such as an ASIC or a FPGA, or an electronic circuit, such as a CPU or a MPU. The storage is a semiconductor memory device, such as a random access memory (RAM) or a flash memory, a hard disk, or an optical disk. The input device is a pointing device, such as a mouse or a trackball, and an input device, such as a keyboard. The display is, for example, a display device, such as a liquid crystal display.

Figure 2:
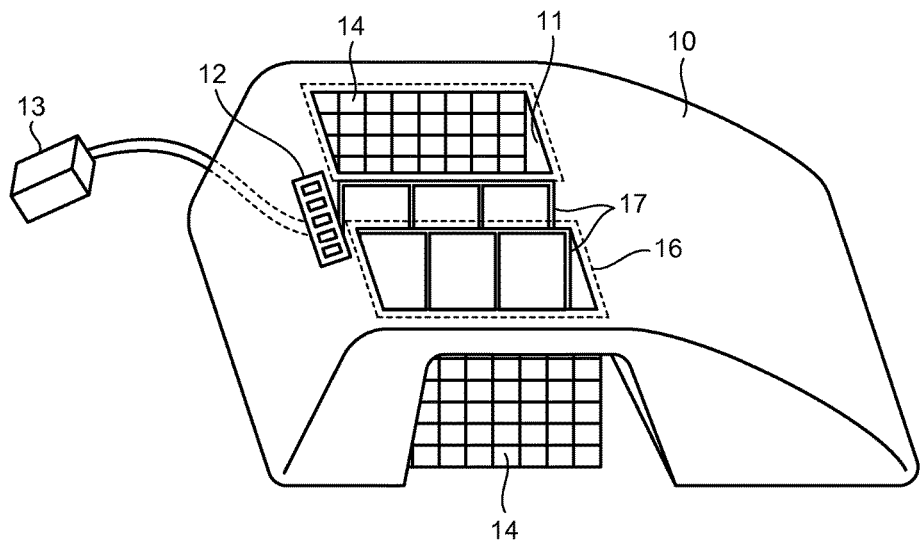
FIG. 2 is a diagram for explaining a breast RF coil according to the first embodiment.

FIG. 2 is a diagram for explaining the breast RF coil 106 according to the first embodiment. As shown in FIG. 2, the breast RF coil 106 includes a supporter 10 that supports the body of the subject P. In the supporter 10, a concave 11 is formed in which a hanging-down breast of the subject P is disposed. The breast RF coil 106 includes circuitry 12 that performs synthesizing and amplifying on the MR signal received by each element, and a connector 13 that transmits the MR signal synthesized and amplified by the circuitry 12 to the receiver 108. The connector 13 is connected to the connector of the couch 109. As shown in FIG. 2, the breast RF coil 106 serves as includes a grid assembly 14 that serves as a puncture needle insertion assembly in which a hole into which a puncture needle is inserted is formed on an outer side surface in the concave 11. According to the first embodiment, the grid assembly 14 is detachably attached to the main unit of the breast RF coil 106 and, after imaging, is detached to be sterilized or disposed.

Figure 3:
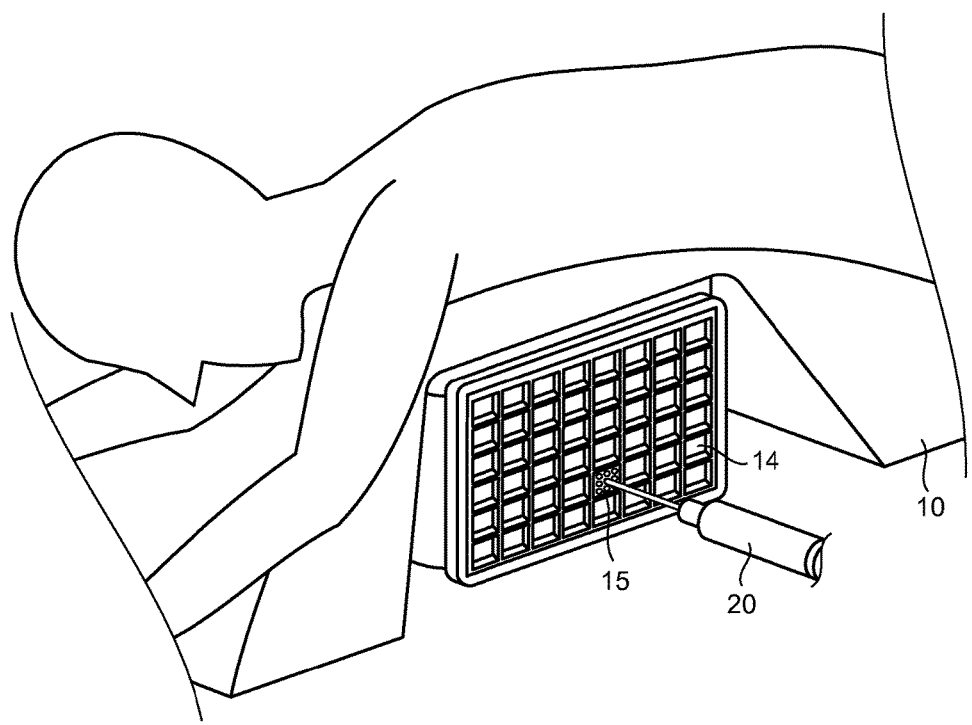
FIG. 3 is a diagram for explaining a grid assembly for puncture according to the first embodiment.

FIG. 3 is a diagram for explaining the grid assembly 14 for puncture according to the first embodiment. In the grid assembly 14, rectangular holes are formed by the grid. In the example shown in FIG. 3, the number of rectangular holes is, for example, 48 and each side of each hole has a size of, for example, 1.8 mm. For puncture, a block 15 for fixing the puncture needle is attached to a hole, from among the rectangular holes, at a position corresponding to the tissue to be sampled. As shown in FIG. 3, the block 15 includes, for example, nine holes and the puncture needle 20 is inserted into one hole in the block 15 and is caused to puncture the breast. The block 15 enables adjustment of the position and angle of puncture.

The coil elements disposed on the breast RF coil 106 will be described. As shown in FIG. 2, the breast RF coil 106 includes an element 16 disposed to surround the outer circumference of the concave 11 on the surface of the supporter 10 and elements 17 that are disposed on an inner side in the concave 11. For example, according to FIG. 2, three elements 17 are disposed in the concave 11. As shown in FIG. 2, the conductor of each element is connected to the circuitry 12.

In the breast RF coil 106, coil elements are disposed also on the grid assembly 14. In the breast RF coil 106, the conductors of the elements are laid to wind in and out among holes while avoiding the rectangular holes formed in the grid assembly 14.

Figure 4:
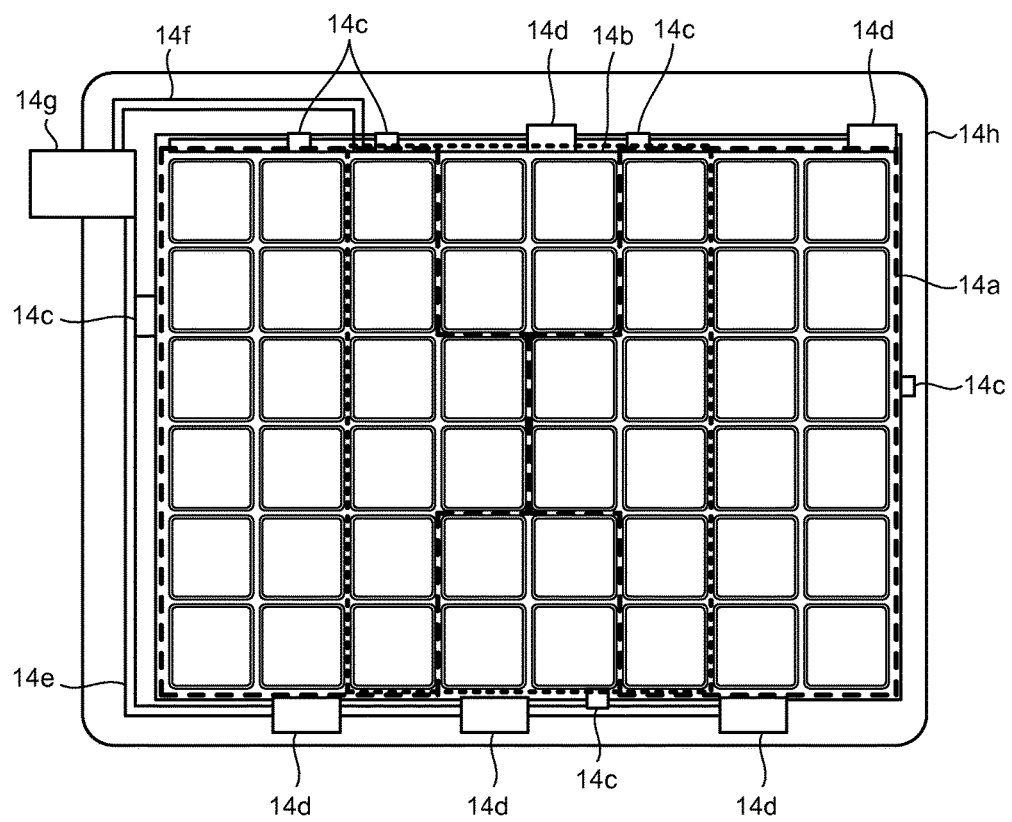
FIG. 4 is a diagram for explaining laying of conductors according to the first embodiment.

FIG. 4 is a diagram for explaining laying of conductors according to the first embodiment. FIG. 4 shows an example where conductor of an element 14a (denoted by dotted line with wide intervals) having the shape of 8 and conductor of a loop element 14b (denoted by dotted line with narrow intervals) are laid while avoiding the rectangular holes. As shown in FIG. 4, in the grid assembly 14, while the rectangular holes are formed, a frame forming the grid structure on the whole plane surface remains as an area other than the holes. The conductor of the element 14a having the shape of 8 and the conductor of the loop element 14b are laid to pass through the frame and are laid while properly meandering within the plane surface to form the shapes of eight and a loop. For example, the conductor of the element 14a having the shape of 8 and the conductor of the loop element 14b are sealed in a resin that forms the frame (including synthesis resin, e.g., plastic) by using a metal insert molding technology.

FIG. 4 shows the case where each element forms a closed loop on the plane surface of the grid structure; however, embodiments are not limited to this. Each element formed on the plane surface of the grid structure may form an open-loop within the plane surface and may form a closed-loop by being electrically connected to electronic parts that are disposed on the outer circumference of the plane surface. Alternatively, each element may be combined with, for example, the element 16 or the element 17 shown in FIG. 2 to form a closed-loop.

Figure 5:
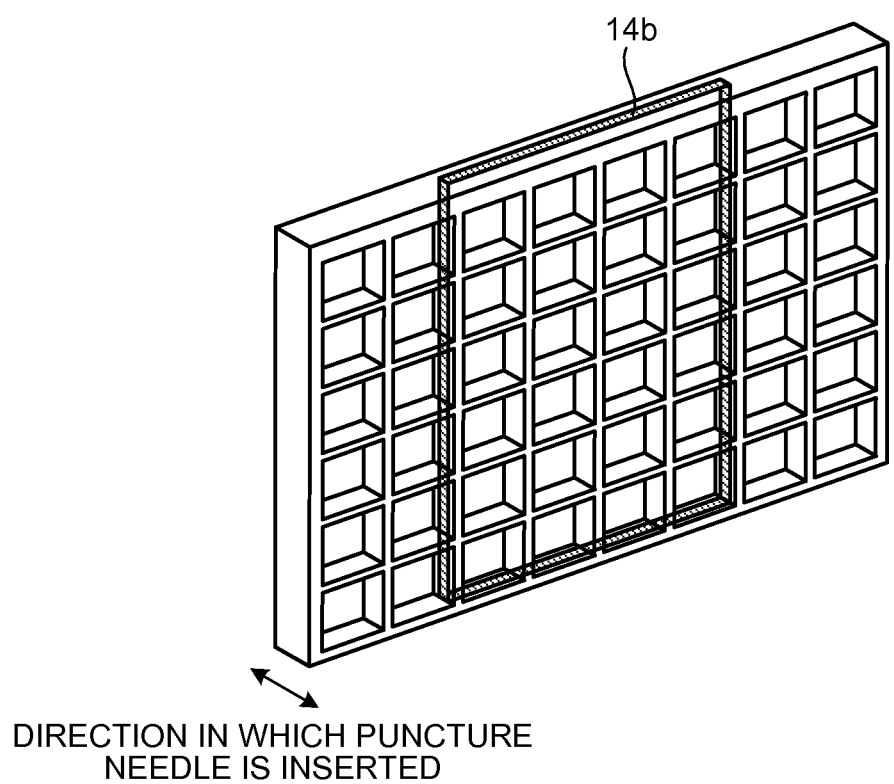
FIG. 5 is a diagram for explaining the thickness of the grid assembly according to the first embodiment.

FIG. 5 is a diagram for explaining the thickness of the grid assembly 14 according to the first embodiment. As shown in FIG. 4, the multiple rectangular holes are formed in the grid assembly 14. From the viewpoint of securing the puncture area, it is preferable that the width of the frame between the holes be small as much as possible. When the line width of the element in a narrower frame, or in order to stably hold the block 15, for example, as shown in FIG. 5, it is preferable that the grid assembly 14 has some thickness in the direction in which the puncture needle is inserted. The thickness is determined in accordance with the design of holes over the grid assembly 14 (the relative relationship with the shape of the holes) and the material. For example, when the width of the frame is small, it is preferable to increase the thickness in the insertion direction. FIG. 5 illustrates the grid assembly 14 transparently for convenience of description and enhances only the conductor of the loop element 14b that is laid within the frame of the grid assembly 14.

For the first embodiment, the case has been described where the conductors of the multiple elements are laid within the frame of the grid assembly 14. In this case, it is preferable that insulation be maintained between elements. For this reason, according to the first embodiment, the grid assembly 14 is formed of layers separated for the respective elements. In other words, the grid assembly 14 is formed by stacking multiple layers in the insertion direction in which the puncture needle is inserted, and the conductors of the elements are laid on the respective layers that are insulated from one another.

Figure 6:
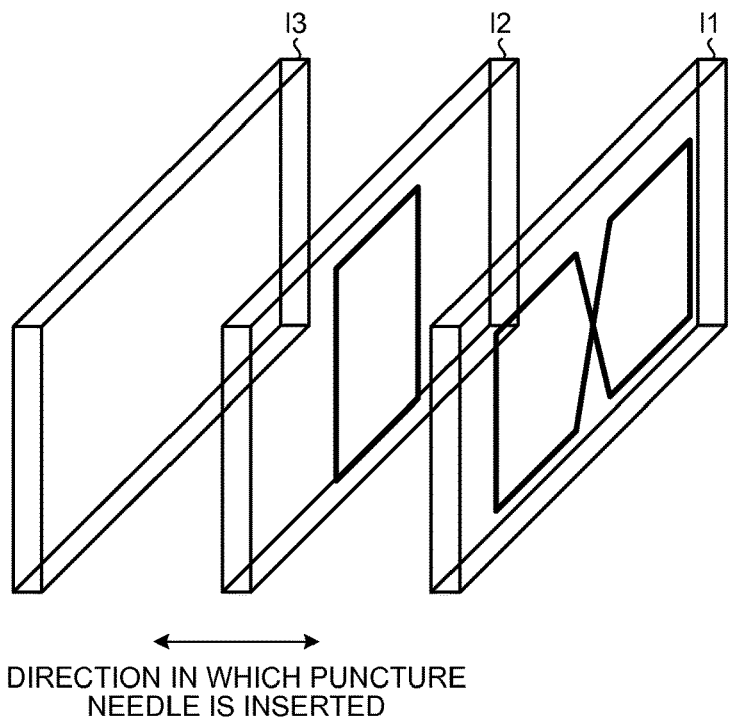
FIG. 6 is a diagram for explaining stacking of elements according to the first embodiment.

FIG. 6 is a diagram for explaining stacking of elements according to the first embodiment. FIG. 6 does not show the rectangular holes formed in the grid assembly 14. For example, the element 14a having the shape of 8 and the loop element 14b are formed on different layers separately. For example, as shown in FIG. 6, the grid assembly 14 is formed by stacking and adhering a resin layer 11 on which the conductor of the element 14a having the shape of 8 is laid, a resin layer 12 on which the conductor of the loop element 14b is laud, and a resin layer 13 on which no element is laid.

Figure 7:
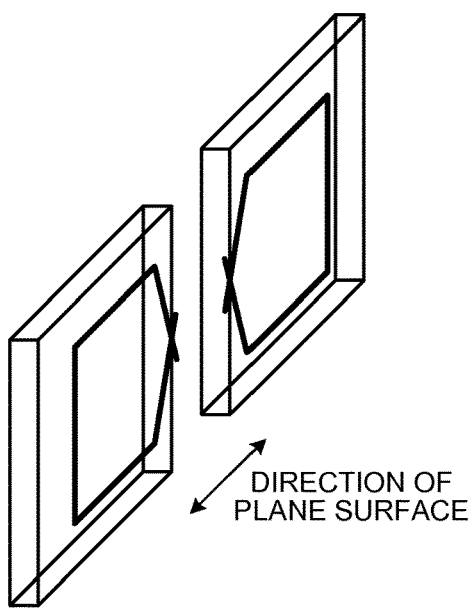
FIG. 7 is a diagram for explaining other exemplary adhesion of elements according to the first embodiment.

FIG. 7 is a diagram for explaining other exemplary adhesion of elements according to the first embodiment. When the conductor of an element having a complicated shape, such as that of the element 14a having the shape of 8, is laid, the element may be further separated into multiple parts and the parts may be adhered in the plane surface direction to form the grid assembly 14.

Such stacking and adhesion enables formation of a complicated array structure of elements while keeping insulation between the elements. Embodiments are not limited to the method of stacking and adhesion shown in FIGS. 6 and 7. It suffices if proper stacking and adhesion are properly performed in accordance with the shape of and positional relationship between elements. For example, the layer 13 shown in FIG. 6 may be omitted. Furthermore, if insulation is kept, multiple elements are not necessarily formed separately and multiple elements may be formed as a single layer.

FIG. 4 will be referred back here. According to the first embodiment, electronic parts are disposed on the outer circumference of the grid assembly 14, i.e., the outer circumference of the group of rectangular holes formed on the plane surface of the grid structure. For example, as shown in FIG. 4, a capacitor 14c and a trap 14d are disposed to surround the plane surface of the grid structure. As shown in FIG. 4, a bias line 14e and a signal line 14f for causing the trap 14d to run are also disposed to surround the plane surface of the grid structure. As shown in FIG. 4, the bias line 14e and the signal line 14f are connected to a connector 14g. The bias line 14e and the signal line 14f are electrically connected to the circuitry 12 of the breast RF coil 106 via the connector 14g. The electronic parts disposed on the outer circumference of the grid assembly 14 are protected with a cladding 14h.

As described above, according to the first embodiment, in the grid assembly 14 in which holes into which the puncture needle is inserted are formed within its plane surface, conductors of coil elements are laid while meandering within the plane surface. For this reason, even when the number of elements is increased for the purpose of, for example, parallel imaging, the elements do not block the puncture area and it is possible to secure a sufficient puncture area. Furthermore, because any shape of element may be selected, there is no limitation that, for example, the diameter of elements has to be increased, which improves the SNR. As a result, it is possible to avoid performance of parallel imaging from lowering and the imaging time from extending.

Second Embodiment

A second embodiment will be described here. According to the above-described first embodiment, it is assumed that the grid assembly 14 is detachably attached to the main unit of the breast RF coil 106 and, after imaging, is sterilized or disposed. This is because, in general, the grid assembly 14 makes a direct contact with the subject P when used. Because the elements in the grid assembly 14 are relatively expensive, disposing the grid assembly 14 has a cost disadvantage. Sterilizing the grid assembly 14 also has a disadvantage that the surface material of the grid assembly 14 deteriorates. In line with this, for the second embodiment, a case will be described where a part that may make a direct contact with the subject P and a part on which elements are disposed are formed to be separable from each other. In other words, according to the second embodiment, the grid assembly 14 is formed to be separable into a part that is disposed on a side at which it makes a direct contact with the subject P and a part that is disposed on a side at which it avoids the contact, and the conductors of the elements are laid on the latter part.

Figure 8:
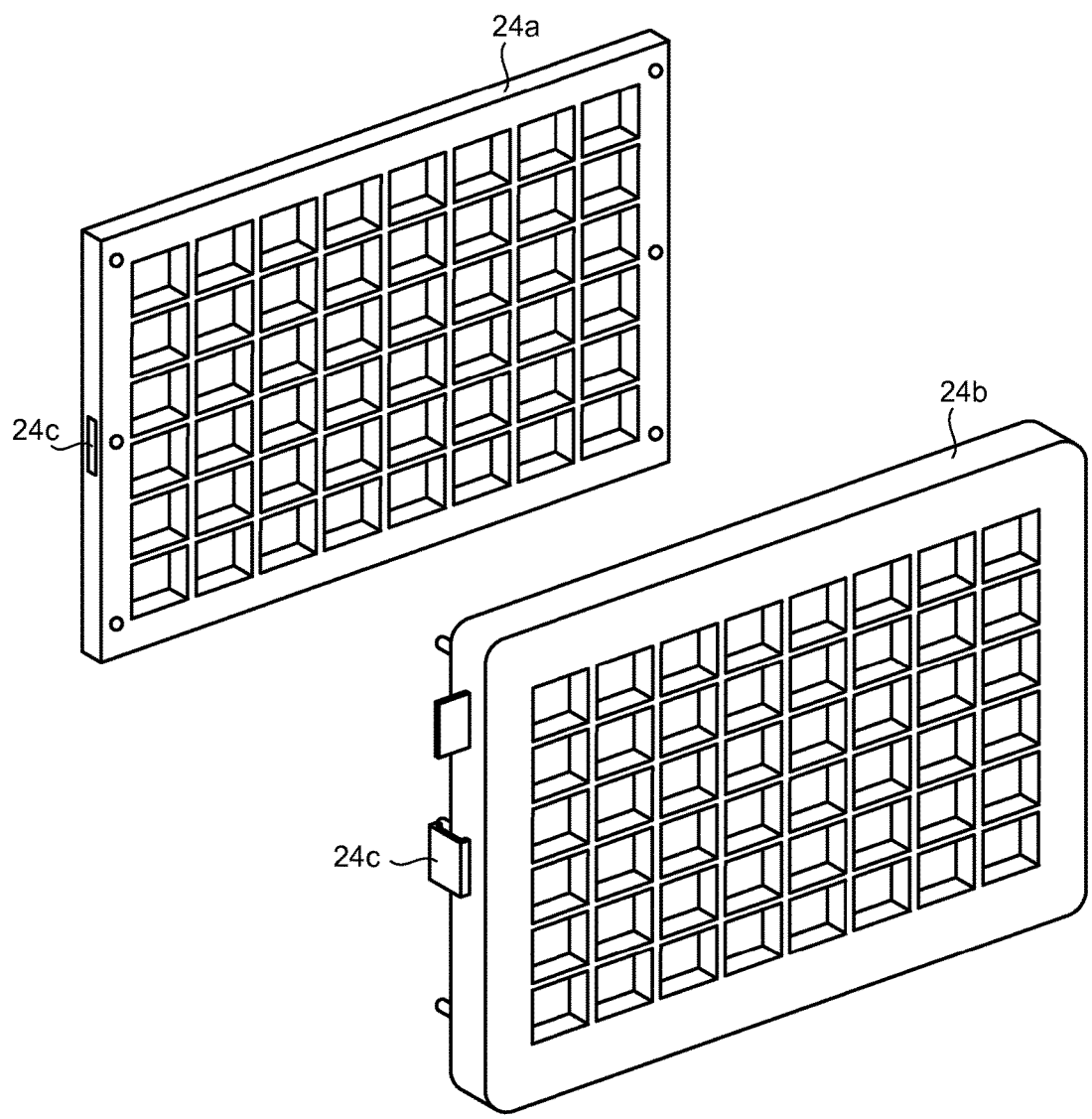
FIG. 8 is a diagram for explaining a grid assembly according to a second embodiment.

FIG. 8 is a diagram for explaining the grid assembly 14 according to the second embodiment. For example, according to the second embodiment, the grid assembly 14 is formed to be separated into a contact part 24a that makes a direct contact with the subject P when used and an element part 24b on which elements are disposed. No element is disposed on the contact part 24a. The contact part 24a and the element part 24b are fixed to each other with a lock part 24c. After imaging, by releasing the lock part 24c, the contact part 24a and the element part 24b are separated from each other and only the contact part 24a is sterilized or disposed.

As described above, according to the second embodiment, the part that may make a direct contact with the subject P and the part on which the elements are disposed are formed to be separable from each other. In this case, the part having made a contact with the subject P is sterilized or disposed thoroughly, which prevents hospital infection caused by, for example, the body fluid of the subject P. Because it is possible to repeatedly use the elements that are relatively expensive, it is possible to prevent deterioration due to sterilization and a cost increase due to disposal.

Other Embodiment

Embodiments are not limited to the above-described embodiments.

For the above-described embodiments, a grid structure is exemplified as the puncture needle insertion assembly on which elements are disposed; however, embodiments are not limited to this. The puncture needle insertion assembly may be modified arbitrarily to be applicable to parts in various shapes other than the above-described block.

Figure 9A:
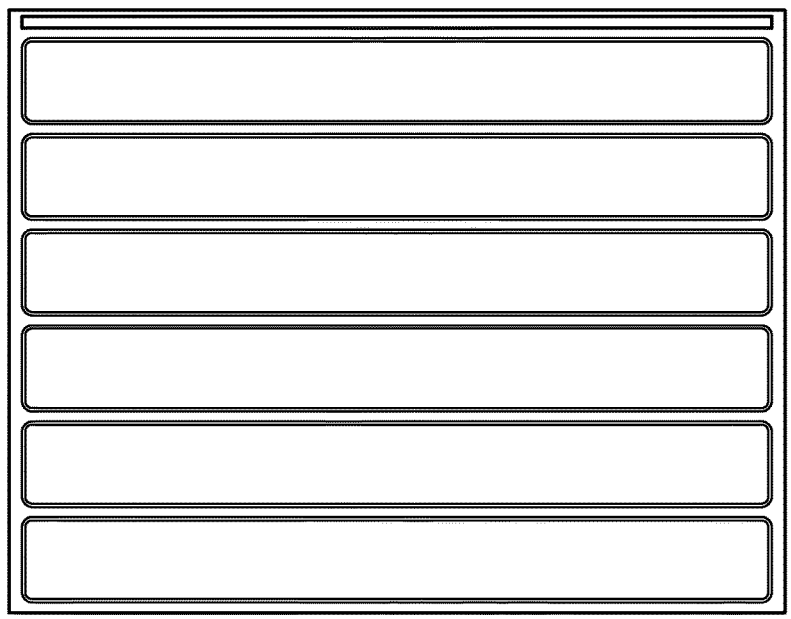
FIGS. 9A and 9B are a diagram for explaining a puncture needle insertion assembly according to another embodiment.
Figure 9B:
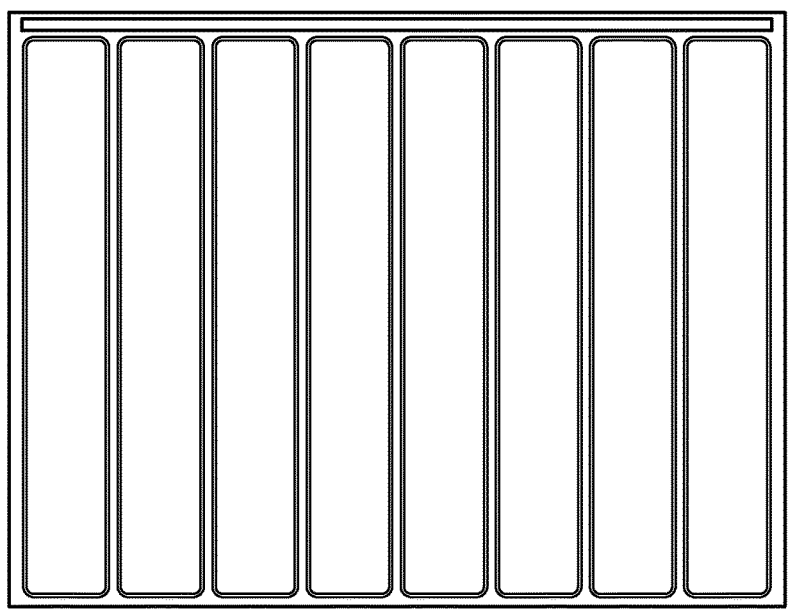

FIGS. 9A and 9B are diagrams for explaining a punctuation needle insertion assembly according to another embodiment. For example, the puncture needle insertion assembly may have a horizontal-stripe structure as shown in FIG. 9A or a vertical-stripe structure as shown in FIG. 9B. The horizontal-stripe structure is a structure in which rectangular holes whose major axis corresponds to the horizontal direction are arranged vertically. The vertical-stripe structure is a structure in which rectangular holes whose major axis corresponds to the vertical direction are arranged horizontally. Also in this case, the conductors of the elements are laid to be properly meandering within the plane surface to avoid the rectangular holes and pass through the frame that forms the horizontal-stripe structure and the vertical-stripe structure. The shape of the holes is not limited to the rectangular shape, and it may be circular or in another shape.

For the above-described embodiments, the case has been described where the conductors of the elements are sealed in the resin of the puncture needle insertion assembly by metal insert molding; however, embodiments are not limited to this. The conductors of the elements may be laid on the resin surface of the puncture needle insertion assembly. In other words, the conductors of the elements are laid on the surface of the frame while properly meandering on the frame to avoid the holes formed in the puncture needle insertion assembly.

The breast RF coil 106 exemplified for the above-described embodiments is an example only, and it is possible to arbitrarily modify the breast RF coil 106 in accordance with, for example, the purpose of imaging. For example, for the above-described embodiments, the case has been described where the two breasts are hung down into the concave 11; however, embodiments are not limited to this. For example, one breast may be hung down into the concave 11. In this case, the puncture needle insertion assembly on which the elements are disposed may be disposed on not only the outer side surface but also the inner side surface in the concave 11.

For the above-described embodiments, the case has been described where the element having the shape of 8 and the loop element are disposed; however, embodiments are not limited to this, and it is possible to arbitrarily change the shape and number of elements.

Furthermore, for the above-described embodiments, the case has been described where the breast coil is exemplified as an RF coil; however, embodiments are not limited to this, and it may be similarly applied to another local coil that is used with the puncture needle insertion assembly attached to the coil.

According to the RF coil according to at least any one of the above-described embodiments, it is possible to properly dispose the elements.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radio frequency (RF) coil for use in a magnetic resonance imaging (MRI) apparatus, said RF coil comprising:
   a puncture needle insertion assembly having a surface with a plurality of defined spaces through which a puncture needle can be inserted,
   wherein the puncture needle insertion assembly includes stacked layers of insulating material, each layer having laid thereon conductor elements of an RF coil that are insulated from conductor elements of an RF coil on another layer and that are laid to meander on a frame between the spaces.

2. The RF coil according to claim 1, wherein, in the puncture needle insertion assembly, the conductor elements are insulated conductors.

3. The RE coil according to claim 1, wherein, in the puncture needle insertion assembly, electronic components of the RF coil are disposed around an outer circumference of a group of the spaces on said surface.

4. The RF coil according to claim 1, wherein the puncture needle insertion assembly has a thickness in a direction transverse to a surface of the assembly determined by a relative relationship with a shape of the spaces.

5. The RF coil according to claim 1, wherein the puncture needle insertion assembly has a first part containing said conductor elements and a second detachable part disposed on a side which is configured to make contact with a subject when in use.

6. The RF coil according to claim 1, wherein the spaces are disposed in a grid pattern.

7. The RF coil according to claim 1, further comprising:
   a couchtop having a concave cavity,
   wherein the conductor elements of the RF coil are disposed along a circumference of the concave cavity.

8. A radio frequency (RF) coil for use in a magnetic resonance imaging (MRI) apparatus, said RF coil comprising:
   a puncture needle insertion assembly having a surface with a plurality of defined spaces through which a puncture needle can be inserted,
   wherein the puncture needle insertion assembly includes a first part having stacked layers of insulating material on which RF coil element conductors are located and a detachable second part disposed on a side that is configured to make contact with a subject when in use, wherein the RF coil element conductors are insulated from one another.

9. A magnetic resonance imaging (MRI) apparatus comprising:
- static and gradient magnetic field generators;
- RF (radio frequency) transmitter and receiver circuits;
- an RF coil that includes (a) a puncture needle insertion assembly having a plurality of defined spaces through which a puncture needle can be inserted within a surface thereof and (b) a plurality of RF coil conductor elements disposed on respectively corresponding stacked layers of insulating material and meandering between the spaces, wherein said conductor elements of the RE coil are insulated from one another; and
- a sequence controller configured to execute an MRI sequence of parallel imaging based on acquiring magnetic resonance signals using said conductor elements of the RF coil.

* * * * *